United States Patent
Kishino et al.

[11] 3,954,919
[45] May 4, 1976

[54] O-ETHYL-S-N-PROPYL-O-(SUBSTITUTED PHENY)-PHOSPHOROTHIOLATES

[75] Inventors: Shigeo Kishino, Tokyo; Akio Kudamatsu; Kozo Skiokawa, both of Kanagawa, Japan

[73] Assignee: Bayer Aktiengesellschaft, Leverkusen, Germany

[22] Filed: Mar. 6, 1974

[21] Appl. No.: 448,587

Related U.S. Application Data

[62] Division of Ser. No. 208,902, Dec. 16, 1971, Pat. No. 3,839,511.

[30] Foreign Application Priority Data
Dec. 26, 1970   Japan.............................. 45-118740

[52] U.S. Cl............................... 260/940; 260/941; 260/942; 260/946; 260/949; 260/954
[51] Int. Cl.²...................... A01N 9/36; C07F 9/18
[58] Field of Search ........... 260/949, 940, 941, 942, 260/946, 954

[56] References Cited
UNITED STATES PATENTS
3,082,239  3/1963  Muhlmann et al.............. 260/954 X
3,742,094  6/1973  Kishino et al....................... 260/940

FOREIGN PATENTS OR APPLICATIONS
98,101  2/1964  Denmark............................ 260/964

*Primary Examiner*—Richard L. Raymond
*Attorney, Agent, or Firm*—Burgess, Dinklage & Sprung

[57]   ABSTRACT

O-ethyl-S-n-propyl-O-(substituted phenyl)-phosphorothiolates of the general formula

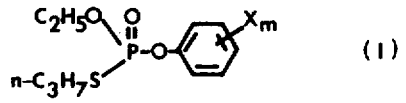

wherein
X is halogen, lower alkyl, nitro, cyano, lower alkylmercapto, lower alkylsulfinyl, lower alkoxycarbonyl or lower alkyl carbonyl, and
$m$ is 1, 2 or 3,
which possess insecticidal, acaricidal and nematocidal properties.

8 Claims, No Drawings

O-ETHYL-S-N-PROPYL-O-(SUBSTITUTED PHENY)-PHOSPHOROTHIOLATES

This is a division of application Ser. No. 208,902, filed Dec. 16, 1971, now U.S. Pat. No. 3,839,511.

The present invention relates to and has for its objects the provision of particular new O-ethyl-S-n-propyl-O-(substituted phenyl)-phosphorothiolates, i.e. those wherein the phenyl group carries 1, 2 or 3 halogen, lower alkyl, nitro, cyano, lower alkylmercapto, lower alkylsulfinyl, lower alkoxycarbonyl or lower alkylcarbonyl groups, which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids, and nematodes, with other and further objects becoming apparent from a study of the within specification and accompanying examples.

It is known that O,S-dialkyl-O-phenylphosphorothiolates exhibit insecticidal activity. However, this activity is so low that they have not been used in spite of being less toxic to warm-blooded animals than the corresponding O,O-dialkyl-O-phenylphosphorothioates.

For example, O,O-dimethyl-O-4-nitrophenylphosphorothioate (Compound A: common name, methylparathion) of the following formula:

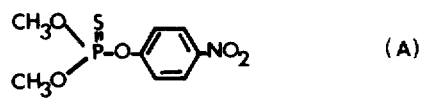

(A)

has strong insecticidal activity and exhibits excellent effects, while the corresponding O,S-dimethyl-4-nitrophenyl phosphorothiolate (Compound B) of the formula:

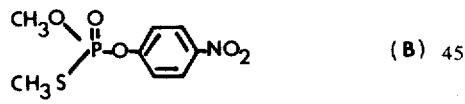

(B)

which has only one-third of the toxicity to warm-blooded animals has unfortunately only one-fiftieth of the insecticidal activity.

As methylparathion is very toxic to warm-blooded animals, much research has been conducted with a view to developing a novel effective insecticide with low toxicity to warm-blooded animals and has resulted in the provision of O,O-dimethyl-O-(3-methyl-4-nitrophenyl)phosphorothioate (Compound C: commercial name, Sumithion) and O,O-dimethyl-O-(3-methyl-4-methylthiophenyl)-phosphorothioate (Compound D: commercial name, lebaycid).

These phosphorothioates have been widely used as insecticides, but difficulty has been found in controlling harmful insects which have acquired resistance to these insecticides. In such circumstances, there is a strong demand for a novel insecticide effective against resistant harmful insects.

The present invention provides compounds which have great insecticidal activity, only slight toxicity for warm-blooded animals and practically no phytotoxicity, so that they can be used for controlling a great variety of harmful insects, such as harmful sucking insects, biting insects, plant parasites, hygiene pest insects and storedgrain insects.

The present invention is based on the surprising discovery that those O-alkyl-S-alkyl-O-phenylphosphorothiolates in which the alkyl groups are different and in which the alkyl attached to the S atom is n-propyl and the O-alkyl is ethyl have excellent insecticidal activity, very much greater for example than if the two alkyls have the same number of carbon atoms or if the alkyl attached to the S atom is alkyl other than n-propyl.

The present invention accordingly provides particular O-ethyl-S-n-propyl-O-phenyl phosphorothiolates of the following general formula:

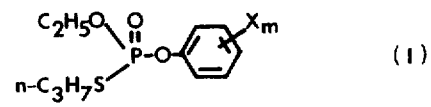

(I)

wherein
X is halogen, lower alkyl, nitro, cyano, lower alkylmercapto, lower alkylsulfinyl, lower alkoxycarbonyl or lower alkyl carbonyl, and
m is 1, 2 or 3.

The invention also provides a process for the production of a compound according to the invention in which
a. a thiol phosphoric acid diester halide of the general formula:

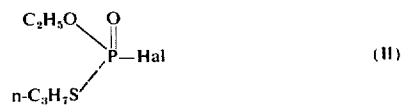

(II)

is reacted with a phenol of the general formula:

(III)

b. a compound of the general formula:

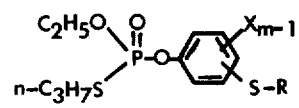

is reacted with an oxidizing agent, or c. a salt of a thiophosphoric acid of the general formula:

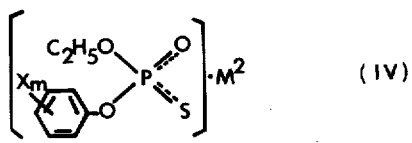

(IV)

is reacted with a halide of the formula:

$$Hal-C_3H_7-n \quad (V)$$

in which formulae
Hal is halogen,
M¹ is hydrogen or a metal or ammonium,
M² is metal or ammonium,
R is lower alkyl, and
X and m have the meanings stated with respect to formula (I).

Process variant (a) is illustrated by the following formula scheme:

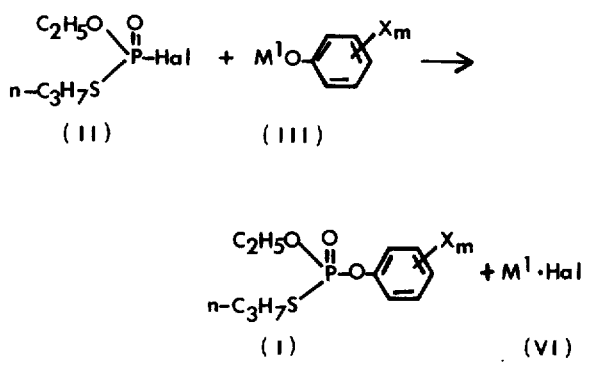

Examples of X are lower alkyl groups such as methyl, ethyl, n-(or iso-) propyl, n-(or iso-, sec.- or tert.-) butyl: halogen atoms such as fluorine, chlorine, bromine or iodine: nitro, cyano, lower alkylmercapto or lower alkylsulfinyl groups: lower alkoxycarbonyl or lower alkylcarbonyl groups.

Hal is preferably chlorine. M¹ may be ammonium, hydrogen, sodium, potassium or lithium.

Examples of the compounds of formula (III) include:
2-(or 3- or 4-)chloro (or bromo)phenol,
2,4-(or 2,5- or 2,6-)dichlorophenol,
2,4-dibromophenol,
2,4,5-(or 2,4,6-)trichlorophenol,
2,5-dichloro-4-bromophenol,
2-(or 3- or 4-)methylphenol,
4-ethylphenol,
2-iso-propylphenol,
4-tert.-butylphenol,
2-sec.-butylphenol,
2,4-(or 3,4- or 3,5-)dimethylphenol,
2-iso-propyl-5-methylphenol,
2-chloro-4-(or 5- or 6-)methylphenol,
4-chloro-2-(or 3-)methylphenol,
2-chloro-4-tert.-butylphenol,
4-chloro-3,5-dimethylphenol,
2,4-dichloro-6-methylphenol,
2-(or 3- or 4-)nitrophenol,
2-(or 3-)chloro-4-nitrophenol,
3-methyl-4-nitrophenol,
3-nitro-4-(or 6-)methylphenol,
2-nitro-4-chlorophenol,
2-nitro-4-methylphenol,
2,6-dichloro-4-nitrophenol,
3-nitro-4-chlorophenol,
2-(or 4-)cyanophenol,
2-chloro-4-cyanophenol,
2-cyano-4-chlorophenol,
2-cyano-4,6-dichlorophenol,
2-(or 4-)ethoxycarbonylphenol,
2-chloro-4-ethoxycarbonylphenol,
2,6-dichloro-4-ethoxycarbonylphenol,
2-methoxycarbonylphenol,
2-ethoxycarbonyl-4-chlorophenol,
2-ethoxycarbonyl-4,6-dichlorophenol,
2-(or 4-)methylcarbonylphenol,
2,6-dichloro-4-methylcarbonylphenol,
2-chloro-4-methylmercaptophenol,
4-methylmercaptophenol,
4-ethylmercaptophenol,
2-methyl-4-methylmercaptophenol,
3-methyl-4-methylmercaptophenol,
3,5-dimethyl-4-methylmercaptophenol,
4-methylsulfinylphenol,
2-methyl-4-methylsulfinylphenol,
3,5-dimethyl-4-methylsulfinylphenol.

Sodium or potassium salts of the corresponding phenols may be used.

In the production of the compounds of this invention according to the above method, the reaction is preferably conducted in a solvent or diluent. For this purpose any inert solvent or diluent may be used.

As the solvent or diluent there may be cited water; aliphatic, alicyclic and aromatic hydrocarbons which may be chlorinated such as hexane, cyclohexane, petroleum ether, ligroin, benzene, toluene, xylene, methylene chloride, chloroform, carbon tetrachloride, mono-, di-, and tri-chloroethylenes, and chlorobenzene; ethers such as diethyl ether, methyl ethyl ether, di-iso-propyl ether, dibutyl ether, ethylene oxide, dioxane and tetrahydrofurane; ketones such as acetone, methyl ethyl ketone, methyl isobutyl ketone; nitriles such as acetonitrile propionitrile and acrylonitrile; alcohols such as methanol, ethanol, isopropanol, butanol and ethylene glycol; esters such as ethyl acetate and amyl acetate; amides such as dimethyl formamide and dimethyl acetamide; and sulfoxides and sulfones such as dimethyl sulfoxide and sulfolane.

This process variant may be carried out in the presence of an acid binder according to need. As the acid binder there may be cited hydroxides, carbonates, bicarbonates and alcoholates of alkali metals and tertiary amines such as triethylamine, diethylaniline and pyridine.

In this process variant, the reaction may be effected at temperatures over a broad range, but generally the reaction is carried out at temperatures ranging from about -20°C to the boiling point of the reaction mixture, preferred temperatures being in the range from about 10 to 100°C.

Process variant (c) is illustrated by the following formula scheme:

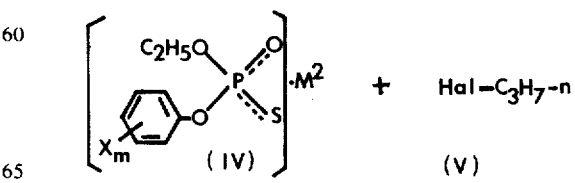

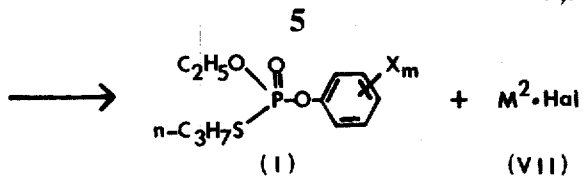

(I)                  (VII)

Examples of the salts of O-ethyl-O-substituted phenyl thiophosphoric acid of the formula (IV) used as starting material include:

O-ethyl-O-[2- (or 3- or 4-)chlorophenyl]-,
O-ethyl-O-[2- (or 4-)bromophenyl]-,
O-ethyl-O-[2- (or 3- or 4-)methylphenyl]-,
O-ethyl-O-(4-ethylphenyl)-,
O-ethyl-O-(2-iso-propylphenyl)-,
O-ethyl-O-(4-tert.-butylphenyl)-,
O-ethyl-O-(2-sec.-butylphenyl)-,
O-ethyl-O-(4-methylmercaptophenyl)-,
O-ethyl-O-(4-ethylmercaptophenyl)-,
O-ethyl-O-(4-methylsulfinylphenyl)-,
O-ethyl-O-[2-(3- or 4-)nitrophenyl]-, l
O-ethyl-O-[2-(or 4-)cyanophenyl]-,
O-ethyl-O-(2-methoxycarbonylphenyl)-,
O-ethyl-O-[2-(or 4-)methylcarbonylphenyl]-,
O-ethyl-O-[2-(or 4-)ethoxycarbonylphenyl]-,
O-ethyl-O-[2,4-(or 2,5- or 2,6-)dichlorophenyl]-,
O-ethyl-O-(2,4-dibromophenyl)-,
O-ethyl-O-[2,4-(3,4- or 3,5-)dimethylphenyl]-,
O-ethyl-O-(2-iso-propyl-5-methylphenyl)-,
O-ethyl-O-(2-chloro-4-methylphenyl)-,
O-ethyl-O-(2-chloro-6-methylphenyl)-,
O-ethyl-O-(2-chloro-5-methylphenyl)-,
O-ethyl-O-(2-methyl-4-chlorophenyl)-,
O-ethyl-O-(3-methyl-4-chlorophenyl)-,
O-ethyl-O-(2-chloro-4-tert.-butylphenyl)-,
O-ethyl-O-(3-methyl-4methylmercaptophenyl)-,
O-ethyl-O-(2-chloro-4-nitrophenyl)-,
O-ethyl-O-(3-chloro-4-nitrophenyl)-,
O-ethyl-O-(3-methyl-4-nitrophenyl)-,
O-ethyl-O-(3-nitro-4-methylphenyl)-,
O-ethyl-O-(2-methyl-5-nitrophenyl)-,
O-ethyl-O-(2-nitro-4-chlorophenyl)-,
O-ethyl-O-(2-nitro-4-methylphenyl)-,
O-ethyl-O-(3-nitro-4-chlorophenyl)-,
O-ethyl-O-(2-chloro-4-cyanophenyl)-,
O-ethyl-O-(2-cyano-4-chlorophenyl)-,
O-ethyl-O-(2-chloro-4-ethoxycarbonylphenyl)-,
O-ethyl-O-(2-ethoxycarbonyl-4-chlorophenyl)-,
O-ethyl-O-(2,6-dichloro-4-methylcarbonylphenyl)-,
O-ethyl-O-(2-chloro-4-methylmercaptophenyl)-,
O-ethyl-O-(2-methyl-4-methylmercaptophenyl)-,
O-ethyl-O-(2-methyl-4-methylsulfinylphenyl)-,
O-ethyl-O-(2,4,5-trichlorophenyl)-,
O-ethyl-O-(2,5-dichloro-4-bromophenyl)-,
O-ethyl-O-(2,4,6-trichlorophenyl)-,
O-ethyl-O-(3,5-dimethyl-4-chlorophenyl)-,
O-ethyl-O-(2,4-dichloro-6-methylphenyl)-,
O-ethyl-O-(2,6-dichloro-4-nitrophenyl)-,
O-ethyl-O-(2-cyano-4,6-dichlorophenyl)-,
O-ethyl-O-(2,6-dichloro-4-ethoxycarbonylphenyl)-,
O-ethyl-O-(2-ethoxycarbonyl-4,6-dichlorophenyl)-,
O-ethyl-O-(3,5-dimethyl-4methylmercaptophenyl)-, or
O-ethyl-O-(3,5-dimethyl-4-methylsulfinylphenyl)-thiophosphoric acid potassium salt and the corresponding sodium and ammonium salts.

Examples of the n-propylhalide of the formula (V) used as starting material include n-propylbromide and the corresponding chlorides.

This process variant may be carried out in the same manner as process variant (a), and the compound of the present invention can be obtained with high purity and in high yield.

As mentioned above, the compounds of the present invention can be used for controlling harmful insects of a broad range such as those belonging to Coleoptera such as
  Rice weevil                Sitophilus oryzae
  Rust beetle                Tribolium castaneum
  28-spotted lady beetle     Epilachana vigintioctopunctata
  Barley wireworm         Agriotes fuscicollis
  Soy bean beetle         Anomala rufocuprea
Lepidoptera such as
  Gypsy moth               Lymantria dispar
  Tent caterpillar          Malacosoma neustria testacea
  Common cabbageworm    Pieris rapae crucivo ra
  Tobacco cutworm        Prodenia litura
  Rice-stem borer         Chilo suppressalis
  Smaller tea tortrix       Adoxophyes orana
  Almond moth             Ephestia cautella
Hemiptera such as
  Green rice leafhopper     Nephotettix cincticeps
  Brown planthopper       Nilaparvata lugens
  Comstock mealybug       Pseudococcus comstocki
  Arrowhead scale         Unaspis yanonensis
  Green peach aphid        Myzus persicae
  Apple aphid              Aphis pomi
  Cabbage aphid           Brevicoryne brassicae
Orthoptera such as
  German cockroach        Blatella germanica
  American cockroach      Periplaneta americana
  African mole cricket      Gryllotalpa africana
Isoptera such as
  Japanese termite         Leucotermes speratus
Diptera such as
  House fly                 Musca domestica vicina
  Yellow fever mosquito    Aedes aegypti
  Seed-cornamaggot        Hylemya platura
  Common mosquito        Culex pipiens
  Malaria mosquito         Anopheles simensis
  Japanese encephalistis mosquito    Culex tritaeniorhynchus
Acarina such as
  Carmine mite            Tetranychus telarius
  Citrus red mite         Panonychus citri
  Japanese citrus red mite    Aculus pelekassi
Nematode such as
  Southern root-knot nematode    Meloidogyne incognita
  Rice white-tip nematode    Aphelenchoides besseyi
  Soy bean cyst nematode    Heterodera glycines The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added to auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbon (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active gents, especially plant protection agents, such as other insecticides, acaricides, and nematocides, or rodenticides, fungicides, bactericides, herbicides, fertilizers, growth-regulating agents, antibiotics, antiviral agents, or attractants, e.g. organic phosphorous acid esters, carbamates, dithio- or (thiol) carbamates, chlorinated compounds, dinitro compounds, organic sulfur or metal compounds, substituted diphenyl ethers, anilides, urea, triazines, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–20%, preferably 0.005–10%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.005–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1,000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids, fungi, bacteria and yeasts, and more particularly methods of combating at least one of insects and acarids, which comprises applying to at least one of correspondingly (a) such insects, (b) such acarids, (c) such nematodes and (d) the corresponding habitat thereof, i.e. the locus to be protected, a correspondingly combative or toxic amount, i.e. an insecticidally, acaricidally or nematocidally effective amount of the particular active compound of the invention alone or together with a carrier vehicle as noted above.

The formulations and ready-to-use preparations may be applied in the usual manner, for instance by spraying (such as liquid spraying), misting, atomizing, dusting, scattering, watering, pouring, fumigating, soil application (such as mixing, sprinkling, vaporizing, irrigating), by surface application (such as painting, banding, dressing), by dipping or in the form of baits.

It will be realized, of course, that the concentration of the particular active compound utilized in admixture with the carrier vehicle will depend upon the intended application. Therefore, in special cases it is possible to go above or below the aforementioned concentration ranges.

The invention is illustrated by the following Examples, comprising preparative Examples 1 to 6, formulation Examples 7 to 12 and test Examples 13 to 19. In the formulation and test Examples, individual compounds according to the invention are identified by numbers corresponding to those in Table 1 following Example 6.

EXAMPLE 1

Synthesis of S-n-propyl-O-ethylchloride phosphorothiolate (a) $\underset{n\text{-}C_3H_7S}{\overset{C_2H_5O}{>}} P \overset{O}{\underset{}{\diagdown}} Cl$ 19.3 of S-n-propyldichloride phosphorothiolate were dissolved in 100 ml of benzene, into which a mixture consisting of 4.6 g of ethanol, 10.1 g of triethylamine and 20 ml of benzene was dropped while stirring at a temperature no higher than 0°C. Upon completion of the addition, the reaction mixture was stirred at room temperature for 2 hours to complete the reaction. Then the reaction mixture was separated by filtration and the filtrate was concentrated by distillation. The residue thus obtained was distilled under reduced pressure, whereby 15 g of S-n-propyl-O-ethylchloride phosphorothiolate was obtained.

Boiling point: 70°–74°C/0.4 mm Hg. Refractive index $n_D^{20} = 1.4901$.

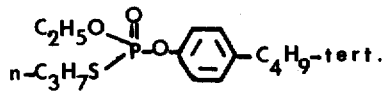

15 g of 4-tert.-butyl phenol were dissolved in 150 ml of benzene, to which 10.1 g of triethylamine were added. 20.3 g of S-n-propyl-O-ethylchloride phosphorothiolate were added dropwise into the mixture while stirring at a temperature no higher than 10°C. Upon completion of the addition, the mixture was stirred for a while at room temperature and was then heated at 65°C for 3 hours with stirring. Upon completion of the reaction, the mixture was washed with water, 1% hydrochloric acid, 1% sodium carbonate and water in the order mentioned and dried over anhydrous sodium sulfate. After removal of benzene by distillation, the residue was distilled under reduced pressure, whereby O-ethyl-O-(4-tert.-butylphenyl)-S-n-propyl phosphorothiolate was obtained in an amount of 25 g.

Boiling point: 155°–156°C/0.07 mm Hg. Refractive index $n_D^{20} = 1.5111$.

EXAMPLE 2

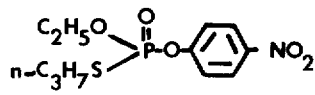

13.9 g of 4-nitrophenol were dissolved in 150 ml of benzene, to which 10.1 g of triethylamine were added. 20.3 g of S-n-propyl O-ethylchloride phosphorothiolate were dropped into the mixture while stirring at a temperature no higher than 10°C. Upon completion of the addition, the mixture was stirred for a while at room temperature and was then heated at 65°C for 3 hours with stirring. Upon completion of the reaction, the mixture was washed with water, 1% hydrochloric acid, 1% sodium carbonate and water in the order mentioned and dried over anhydrous sodium sulfate. After removal of benzene by distillation, the residue was distilled under reduced pressure, whereby O-ethyl-O-(4-nitrophenyl)-S-n-propyl phosphorothiolate was obtained in an amount of 24 g.

Boiling point: 159°–161°C/0.025 mm Hg. Refractive index $n_D^{20} = 1.5424$.

EXAMPLE 3

Synthesis of the potassium salt of O-ethyl-O-(4-methylthiophenyl)thiophosphoric acid

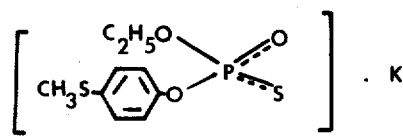

41.g of potassium hydroxide were dissolved in 200 ml of water, to which 250 ml of dioxane were added. While stirring vigorously, 102 g of O-ethyl-O-(4-methylthiophenyl)thionophosphoryl chloride were dropped in at 30°–40°C. Upon completion of the adding, the mixture was further stirred continuously for 1 hour at 60°C to complete the reaction.

The dioxane and water were distilled off under reduced pressure and the residue was dissolved in water again. Benzene was then added to the solution. The mixture was shaken. The aqueous part was concentrated under reduced pressure and the residue was dissolved in acetone and the inorganic salt was separated by filtration. After the acetone had been distilled off, toluene was added to the residue and the precipitate formed was separated by filtration, whereby 85 g of crude potassium O-ethyl-O-(4-methylthiophenyl)-S-n-propyl phosphorothiolate were obtained.

EXAMPLE 3

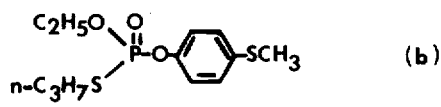 (b)

30.2 g of the potassium salt of O-ethyl-O-(4-methylthiophenyl) thiophosphoric acid were dissolved in 80 ml of alcohol, to which 13 g of n-propylbromide were added. The mixture was stirred for 4 hours at 60°C and the inorganic salt formed was separated by filtration. After the alcohol had been distilled off the residue was dissolved in benzene and washed with water, 1% sodium carbonate and water in the order mentioned. After drying with Na₂SO₄, the benzene was distilled off and the residue was distilled under reduced pressure, whereby 25 g of O-ethyl-O-(4-methylthiophenyl)-S-n-propyl phosphorothiolate were obtained.

Boiling point: 145° – 152°C/0.05 mmHg. Refractive index $n_D^{20} = 1.5515$.

EXAMPLE 4

Synthesis of potassium O-ethyl-O-(2,4-dichlorophenyl)-thiophosphate

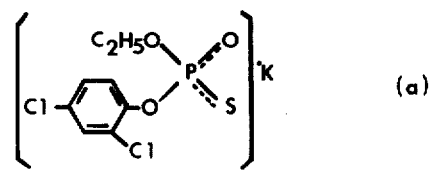 (a)

34 g of potassium hydroxide were dissolved in 200 ml of water, to which 200 ml of dioxane were added. While the mixture was being vigorously stirred, 92 g of O-ethyl-O-(2,4-dichlorophenyl)thiophosphoryl chloride were dropped in at 30° – 40°C. Upon completion of the addition, the temperature was gradually raised and the mixture was further stirred continuously for 1 hour at 60° – 70°C to complete the reaction.

The dioxane and water were distilled off under reduced pressure and the residue was dissolved in acetone and the inorganic salt was separated by filtration. After distilling acetone off, toluene and n-hexane were added to the residue and the precipitate formed was separated by filtration, whereby 75 g of crude potassium O-ethyl-O-(2,4-dichlorophenyl) thiophosphate were obtained.

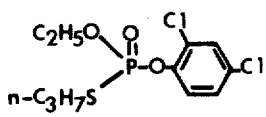
(b)

32.5 g of potassium salt of O-ethyl-O-(2,4-dichlorophenyl) thiophosphoric acid were dissolved in 70 ml of alcohol, to which 13 g of n-propyl bromide were added. The mixture was stirred for 3 hours at 70°C and the inorganic salt formed was separated by filtration. After the alcohol had been distilled off, the residue was dissolved in benzene and washed with water and 1% sodium carbonate. After drying with $Na_2SO_4$, the benzene was distilled off and the residue was distilled under reduced pressure whereby 27 g of O-ethyl-O-(2,4-dichlorophenyl)-S-n-propylphosphorothiolate were obtained.

Boiling point: 155° – 165°C/0.25 mmHg. Refractive index $n_D^{20} = 1.5362$.

EXAMPLE 5

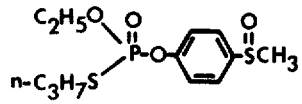

15.3 g of O-ethyl-O-(4-methylthiophenyl)-S-n-propylphosphorothiolate, produced in Example 3 (b), were dissolved in 60 ml of glacial acetic acid. 6 g of 30% hydrogen peroxide solution were added dropwise while the reaction temperature was maintained at 20° – 30°C with external cooling. After the completion of the addition, the reaction mixture was stirred for 1 hour and then heated at 40°C for 30 minutes to complete the reaction. The reaction mixture was diluted with water and benzene and then it was shaken. The benzene layer was washed sequentially with water, 1% sodium carbonate solution and water, and then dried over anhydrous sodium sulfate. After the benzene had been distilled off, 14 g of light yellowish oily O-ethyl-O-(4-methylsulfinylphenyl)-S-n-propylphosphorothiolate, $n_D^{20} = 1.5496$, were obtained.

EXAMPLE 6

The following Table 1 contains a list of compounds according to the invention. These compounds can be prepared by methods analogous to those described in Example 1 – 5.

Table 1

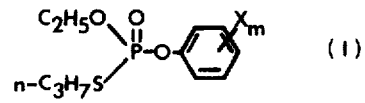

| Compound | $X_m$ | Physical Properties | |
|---|---|---|---|
| 1 | 2-Cl | b.p. 132 – 143°C/0.2mmHg | $n_D^{20}$ 1.5276 |
| 2 | 3-Cl | b.p. 130 – 136°C/0.1mmHg | $n_D^{20}$ 1.5243 |
| 3 | 4-Cl | | $n_D^{20}$ 1.5262 |
| 4 | 2-Br | b.p. 140 – 147°C/0.1mmHg | $n_D^{20}$ 1.5467 |
| 5 | 4-Br | b.p. 136 – 140°C/0.15mmHg | $n_D^{20}$ 1.5503 |
| 6 | 2-CH₃ | b.p. 116 – 119°C/0.08mmHg | $n_D^{20}$ 1.5192 |
| 7 | 3-CH₃ | b.p. 132 – 139°C/0.08mmHg | $n_D^{20}$ 1.5209 |
| 8 | 4-CH₃ | b.p. 125 – 133°C/0.1mmHg | $n_D^{20}$ 1.5191 |
| 9 | 4-C₂H₅ | b.p. 133 – 137°C/0.1mmHg | $n_D^{20}$ 1.5183 |
| 10 | 2-iso-C₃H₇ | b.p. 119 – 121°C/0.08mmHg | $n_D^{20}$ 1.5120 |
| 11 | 4-tert-C₄H₉ | b.p. 155 – 156°C/0.07mmHg | $n_D^{20}$ 1.5111 |
| 12 | 2-sec-C₄H₉ | b.p. 145 – 149°C/0.1mmHg | $n_D^{20}$ 1.5103 |
| 13 | 4-CH₃S— | b.p. 145 – 152°C/0.05mmHg | $n_D^{20}$ 1.5515 |
| 14 | 4-C₂H₅S— | b.p. 148 – 153°C/0.1mmHg | $n_D^{20}$ 1.5483 |
| 15 | 4-CH₃S(O)— | | $n_D^{20}$ 1.5496 |
| 16 | 4-NO₂ | b.p. 159 – 161°C/0.25mmHg | $n_D^{20}$ 1.5424 |
| 17 | 3-NO₂ | b.p. 153 – 158°C/0.2mmHg | $n_D^{20}$ 1.5421 |
| 18 | 2-NO₂ | b.p. 151 – 155°C/0.09mmHg | $n_D^{20}$ 1.5351 |
| 19 | 4-CN | b.p. 145 – 149°C/0.15mmHg | $n_D^{20}$ 1.5293 |
| 20 | 2-CN | b.p. 143 – 147°C/0.15mmHg | $n_D^{20}$ 1.5290 |
| 21 | 4-C₂H₅OC(O)— | b.p. 160 – 162°C/0.25mmHg | $n_D^{20}$ 1.5152 |

Table 1-continued

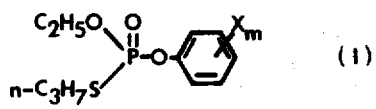

| Compound | $X_m$ | Physical Properties | |
|---|---|---|---|
| 22 | 2-CH₃OC(=O)— | b.p. 153 – 156°C/0.25mmHg | $n_D^{20}$ 1.5193 |
| 23 | 2-C₂H₅OC(=O)— | b.p. 156 – 159°C/0.2mmHg | $n_D^{20}$ 1.5137 |
| 24 | 4-CH₃C(=O)— | b.p. 166 – 169°C/0.15mmHg | $n_D^{20}$ 1.5365 |
| 25 | 2-CH₃C(=O)— | b.p. 155 – 157°C/0.1mmHg | $n_D^{20}$ 1.5388 |
| 26 | 2,4-Cl₂ | b.p. 155 – 165°C/0.25mmHg | $n_D^{20}$ 1.5362 |
| 27 | 2,5-Cl₂ | b.p. 141 – 146°C/0.1mmHg | $n_D^{20}$ 1.5419 |
| 28 | 2,6-Cl₂ | b.p. 141 – 145°C/0.15mmHg | $n_D^{20}$ 1.5477 |
| 29 | 2,4-Br₂ | b.p. 154 – 159°C/0.06mmHg | $n_D^{20}$ 1.5688 |
| 30 | 2,4-(CH₃)₂ | b.p. 128 – 131°C/0.1mmHg | $n_D^{20}$ 1.5160 |
| 31 | 3,4-(CH₃)₂ | b.p. 130 – 132°C/0.08mmHg | $n_D^{20}$ 1.5270 |
| 32 | 3,5-(CH₃)₂ | b.p. 121 – 123°C/0.05mmHg | $n_D^{20}$ 1.5178 |
| 33 | 2-iso-C₃H₇, 5-CH₃ | b.p. 125 – 128°C/0.07mmHg | $n_D^{20}$ 1.5103 |
| 34 | 2-Cl, 4-CH₃ | b.p. 144 – 151°C/0.1mmHg | $n_D^{20}$ 1.5291 |
| 35 | 2-Cl, 6-CH₃ | b.p. 133 – 140°C/0.15mmHg | $n_D^{20}$ 1.5302 |
| 36 | 2-Cl, 5-CH₃ | b.p. 130 – 134°C/0.15mmHg | $n_D^{20}$ 1.5312 |
| 37 | 4-Cl, 2-CH₃ | b.p. 132 – 136°C/0.1mmHg | $n_D^{20}$ 1.5328 |
| 38 | 4-Cl, 3-CH₃ | b.p. 145 – 151°C/0.2mmHg | $n_D^{20}$ 1.5281 |
| 39 | 2-Cl, 4-tert-C₄H₉ | b.p. 144 – 146°C/0.1mmHg | $n_D^{20}$ 1.5230 |
| 40 | 3-CH₃, H—CH₃S— | b.p. 158 – 160°C/0.1mmHg | $n_D^{20}$ 1.5609 |
| 41 | 2-Cl, 4-NO₂ | b.p. 160 – 162°C/0.1mmHg | $n_D^{20}$ 1.5455 |
| 42 | 3-Cl, 4-NO₂ | b.p. 170 – 175°C/0.25mmHg | $n_D^{20}$ 1.5450 |
| 43 | 3-CH₃, 4-NO₂ | b.p. 164 – 168°C/0.07mmHg | $n_D^{20}$ 1.5400 |
| 44 | 3-NO₂, 4-CH₃ | b.p. 147 – 152°C/0.1mmHg | $n_D^{20}$ 1.5308 |
| 45 | 2-CH₃, 5-NO₂ | b.p. 160 – 164°C/0.06mmHg | $n_D^{20}$ 1.5373 |
| 46 | 2-NO₂,4-Cl | b.p. 155 – 157°C/0.08mmHg | $n_D^{20}$ 1.5479 |
| 47 | 2-NO₂, 4-CH₃ | b.p. 156 – 157°C/0.15mmHg | $n_D^{20}$ 1.5318 |
| 48 | 3-NO₂, 4-Cl | b.p. 160 – 164°C/0.1mmHg | $n_D^{20}$ 1.5471 |
| 49 | 2-Cl, 4-CN | b.p. 157 – 161°C/0.1mmHg | $n_D^{20}$ 1.5544 |
| 50 | 2-CN, 4-Cl | b.p. 145 – 147°C/0.06mmHg | $n_D^{20}$ 1.5460 |
| 51 | 2-Cl, 4-C₂H₅OC(=O)— | b.p. 160 – 164°C/0.2mmHg | $n_D^{20}$ 1.5289 |
| 52 | 2-C₂H₅OC(=O)—, 4-Cl | b.p. 160 – 164°C/0.15mmHg | $n_D^{20}$ 1.5216 |
| 53 | 2,6-Cl₂, 4-CH₃C(=O)— | b.p. 173 – 176°C/0.15mmHg | $n_D^{20}$ 1.5462 |
| 54 | 2-CH₃, 4-CH₃S— | b.p. 156 – 160°C/0.05mmHg | $n_D^{20}$ 1.5509 |
| 55 | 2-CH₃, 4-CH₃S(=O)— | | $n_D^{20}$ 1.5489 |
| 56 | 2,4,5-Cl₃ | b.p. 142 – 148°C/0.15mmHg | $n_D^{20}$ 1.5480 |
| 57 | 2,5-Cl₂, 4-Br | b.p. 161 – 165°C/0.15mmHg | $n_D^{20}$ 1.5674 |
| 58 | 2,4,6-Cl₃ | b.p. 143 – 145°C/0.08mmHg | $n_D^{20}$ 1.5496 |
| 59 | 3,5-(CH₃)₂, 4-Cl | b.p. 144 – 148°C/0.1mmHg | $n_D^{20}$ 1.5690 |
| 60 | 2,4-Cl₂, 6-CH₃ | b.p. 138 – 140°C/0.1mmHg | $n_D^{20}$ 1.5408 |
| 61 | 2,6-Cl₂, 4-NO₂ | b.p. 181 – 185°C/0.12mmHg | $n_D^{20}$ 1.5660 |
| 62 | 2-CN, 4,6-Cl₂ | b.p. 172 – 175°C/0.15mmHg | $n_D^{20}$ 1.5569 |
| 63 | 2,6-Cl₂, 4-C₂H₅OC(=O)— | b.p. 176 – 180°C/0.1mmHg | $n_D^{20}$ 1.5347 |
| 64 | 2-C₂H₅OC(=O)—, 4,6-Cl₂ | b.p. 169 – 171°C/0.15mmHg | $n_D^{20}$ 1.5341 |
| 65 | 4-CH₃S—, 3,5-(CH₃)₂ | b.p. 148 – 150°C/0.05mmHg | $n_D^{20}$ 1.5470 |
| 66 | 4-CH₃S(=O)—, 3,5-(CH₃)₂ | | $n_D^{20}$ 1.5524 |
| 67 | 2-Cl, 4-CH₃S | b.p. 153 – 158°C/0.1mmHg | $n_D^{20}$ 1.5650 |

EXAMPLE 7

Wettable powder:

15 parts by weight of compound No. 26, 80 parts by weight of a mixture of diatomaceous earth and clay (1:5) and 5 parts by weight of the emulsifier "Runnox" (polyoxyethylene alkylaryl ether) are mixed and crushed to give a wettable powder. This formulation may be diluted with water to a concentration of 0.05% and may be applied by spraying on insects and/or their habitat.

EXAMPLE 8

Emulsifiable concentrate:

30 parts by weight of compound No. 13, 30 parts by weight of xylene, 30 parts by weight of "Kawakasol" (aliphatic hydrocarbons with a high boiling point) and 10 parts by weight of the emulsifier "Sorpol" (polyoxyethylene alkylaryl ether) are mixed and stirred to give an emulsifiable concentrate. This formulation may be diluted with water to a concentration of 0.05% and may be applied by spraying on insects and/or their habitat.

EXAMPLE 9

Dust 2 parts by weight of compound No. 21 and 98 parts by weight of a mixture of talc and clay (1:3) are mixed and crushed to give a dust. This formulation may be applied by dusting on insects and/or their habitat.

EXAMPLE 10

Dust 1.5 parts by weight of compound No. 5, 2 parts by weight of isopropyl hydrogen phosphate (PAP) and 96.5 parts by weight of a mixture of talc and clay (1:3) are mixed and crushed to give a dust. This formulation may be applied by dusting on insects and/or their habitat.

EXAMPLE 11

Granule 10 parts by weight of compound No. 16, 10 parts by weight of bentonite, 78 parts by weight of a mixture of talc and clay (1:3) and 2 parts by weight of lignin sulphite are mixed. To this mixture 25 parts by weight of water are added and then the mixture is kneaded. It is cut into granules of about 20 to 40 mesh by means of a granulating machine. The granules are then dried at a temperature of 40° to 50°C to give a granular formulation. This formulation may be applied by scattering on insects and/or their habitat.

EXAMPLE 12

Oil 0.5 part by weight of compound No. 40, 20 parts by weight of Versicoal AR-50 (aromatic hydrocarbons with a high boiling point) and 79.5 parts by weight of Deobase (deodorized kerosene) are mixed and stirred to give an oily formulation. This formulation may be applied by spraying on insects and/or their habitat.

EXAMPLE 13

Tobacco cutworm or cotton leaf worm (Prodenia litura) larvae test

Solvent: 3 parts by weight of dimethyl formamide
Emulsifier: 1 part by weight of alkylaryl polyglycol ether To prepare a suitable preparation of the active compound, 1 part by weight of the active compound was thoroughly mixed with the stated amount of solvent and the emulsifier. The emulsifiable concentrate obtained was then diluted with water to the prescribed concentration.

Testing method

Sweet potato leaves were dipped in the preparation of the active compound diluted to the prescribed concentration and were dried and put in a Petri dish of 9 cm diameter. 10 tobacco cutworm larvae were then placed in the dish. The dish was kept in a constant temperature chamber at 28°C. After 24 hours, the number of dead insects was counted and the killing ratio was calculated. The results are shown in Table 2.

Table 2

Test results against *Prodenia litura* larvae

| Compound No. | Killing Ratio (%) Active Ingredient Concentration | | |
|---|---|---|---|
| | 1000ppm | 300ppm | 100ppm |
| 1 | 100 | 100 | 100 |
| 2 | 100 | 100 | 80 |
| 3 | 100 | 100 | 100 |
| 4 | 100 | 100 | 90 |
| 5 | 100 | 100 | 100 |
| 6 | 100 | 100 | 100 |
| 7 | 100 | 100 | 60 |
| 8 | 100 | 90 | — |
| 9 | 100 | 100 | — |
| 10 | 100 | 100 | 60 |
| 11 | 100 | 100 | 50 |
| 12 | 100 | 100 | — |
| 13 | 100 | 100 | 100 |
| 14 | 100 | 100 | 100 |
| 15 | 100 | 100 | 100 |
| 16 | 100 | 100 | 100 |
| 17 | 100 | 100 | 100 |
| 18 | 100 | 100 | — |
| 19 | 100 | 100 | 100 |
| 20 | 100 | 100 | — |
| 21 | 100 | 100 | 90 |
| 22 | 100 | 100 | 100 |
| 23 | 100 | 100 | 90 |
| 24 | 100 | 100 | — |
| 25 | 100 | 100 | 60 |
| 26 | 100 | 100 | 100 |
| 27 | 100 | 100 | 100 |
| 28 | 100 | 100 | 100 |
| 29 | 100 | 100 | 80 |
| 30 | 100 | 100 | 90 |
| 31 | 100 | 90 | — |
| 32 | 100 | 100 | 100 |
| 33 | 100 | 100 | 100 |
| 34 | 100 | 100 | 100 |
| 35 | 100 | 100 | 80 |
| 36 | 100 | 100 | 80 |
| 37 | 100 | 100 | 100 |
| 38 | 100 | 100 | 100 |
| 39 | 100 | 100 | 100 |
| 40 | 100 | 100 | 100 |
| 41 | 100 | 80 | 50 |
| 42 | 100 | 100 | 90 |
| 43 | 100 | 100 | 90 |
| 44 | 100 | 90 | — |
| 45 | 100 | 100 | 60 |
| 46 | 100 | 100 | — |
| 47 | 100 | 100 | 80 |
| 48 | 100 | 100 | 60 |
| 49 | 100 | 100 | 100 |
| 50 | 100 | 100 | 100 |
| 51 | 100 | 100 | 60 |
| 52 | 100 | 100 | 90 |
| 53 | 100 | 100 | 80 |
| 54 | 100 | 100 | — |
| 55 | 100 | 100 | — |
| 56 | 100 | 100 | 100 |
| 57 | 100 | 100 | 100 |
| 58 | 100 | 100 | 100 |
| 59 | 100 | 100 | 80 |
| 60 | 100 | 100 | 100 |
| 61 | 100 | 100 | 80 |
| 62 | 100 | 100 | 80 |
| 63 | 100 | 100 | 50 |
| 64 | 100 | 90 | — |
| 65 | 100 | 100 | — |
| 66 | 100 | 100 | — |
| 67 | 100 | 100 | 90 |
| DFI* (commercially available comparison) | 100 | 25 | 0 |
| MPP** | | | |

Table 2-continued

| Compound No. | Test results against *Prodenia litura* larvae Killing Ratio (%) Active Ingredient Concentration | | |
|---|---|---|---|
| | 1000ppm | 300ppm | 100ppm |
| (commercially available comparison) | 30 | 0 | 0 |
| Untreated control | 0 | | |

*DEP: O,O-dimethyl-1-hydroxy-2,2,2-trichloroethyl-phosphonate
*MPP: O,O-dimethyl-O-[(4-methylmercapto-3-methyl)phenyl] phosphorothioate

EXAMPLE 14

Fall webworm (*Hyphantria cunea*) larvae test

Testing method

Mulberry leaves were dipped in the preparation of the active compound diluted to the prescribed concentration prepared in the same manner as in Example 13, and after drying in air, were placed in a Petri dish of 9 cm diameter. 10 fall webworms were then placed in the dish and the dish was kept in a constant temperature chamber at 25°C. After 24 hours, the number of dead insects was counted and the killing ratio was calculated. The results are shown in Table 3.

Table 3

| Compound No. | Test results against *Hyphantria cunea* larvae Killing Ratio (%) Active ingredient concentration | | |
|---|---|---|---|
| | 1000ppm | 300ppm | 100ppm |
| 1 | 100 | 100 | 100 |
| 3 | 100 | 100 | 100 |
| 5 | 100 | 80 | 60 |
| 10 | 100 | 90 | — |
| 11 | 100 | 100 | 80 |
| 13 | 100 | 100 | 90 |
| 16 | 100 | 100 | 90 |
| 17 | 100 | 100 | — |
| 18 | 100 | 64 | 60 |
| 19 | 100 | 90 | 40 |
| 20 | 100 | 100 | 90 |
| 21 | 100 | 90 | 50 |
| 23 | 100 | 100 | 60 |
| 24 | 100 | 100 | 60 |
| 26 | 100 | 100 | 100 |
| 27 | 100 | 100 | 60 |
| 28 | 100 | 80 | 50 |
| 30 | 100 | 100 | — |
| 32 | 100 | 100 | 100 |
| 36 | 100 | 100 | — |
| 37 | 100 | 100 | 90 |
| 38 | 100 | 100 | 80 |
| 39 | 100 | 100 | 90 |
| 40 | 100 | 100 | 100 |
| 44 | 100 | 70 | 60 |
| 47 | 100 | 100 | — |
| 54 | 100 | 100 | 100 |
| 55 | 100 | 100 | 100 |
| 56 | 100 | 100 | 70 |
| 58 | 100 | 100 | — |
| 60 | 100 | 100 | 80 |
| 65 | 100 | 100 | 100 |
| 66 | 100 | 100 | 100 |
| 67 | 100 | 90 | 80 |
| MPP (commercially available comparison) | 90 | 0 | 0 |

Table 3-continued

| Compound No. | Test results against *Hyphantria cunea* larvae Killing Ratio (%) Active ingredient concentration | | |
|---|---|---|---|
| | 1000ppm | 300ppm | 100ppm |
| Untreated control | 0 | | |

EXAMPLE 15

Rice stem borer (*Chilo suppressalis*) larvae test

Testing method

Egg masses of the rice stem borer were attached to rice, at the tillering stage, planted in a pot of 12 cm diameter, and on the 7th day from the hatching, 40 ml of the preparation of the active compound diluted to the prescribed concentration (prepared in the same manner as in Example 13) were sprayed on to the rice. The rice was kept in a greenhouse. Three days later, the treated stem was examined by breaking it and the killing ratio was calculated from the surviving borers and killed borers. The results are shown in Table 4.

Table 4

| Compound No. | Test results against *Chilo suppressalis* larvae Killing Ratio (%) Active Ingredient Concentration 250ppm | Compound No. | Killing Ratio (%) Active Ingredient Concentration 250ppm |
|---|---|---|---|
| 1 | 100 | 41 | 100 |
| 3 | 100 | 44 | 100 |
| 5 | 100 | 47 | 100 |
| 6 | 100 | 50 | 100 |
| 11 | 87.7 | 51 | 100 |
| 13 | 100 | 52 | 100 |
| 15 | 100 | 53 | 100 |
| 16 | 98.6 | 54 | 100 |
| 18 | 100 | 55 | 100 |
| 19 | 100 | 56 | 100 |
| 20 | 100 | 58 | 94.7 |
| 21 | 100 | 60 | 100 |
| 23 | 95.5 | 65 | 100 |
| 24 | 100 | 66 | 100 |
| 26 | 100 | | |
| 27 | 100 | | |
| 28 | 100 | DEP (commercially available comparison) | 95 |
| 30 | 95.4 | | |
| 32 | 100 | | |
| 37 | 100 | | |
| 38 | 100 | Untreated control | 0 |
| 39 | 99 | | |
| 40 | 96.4 | | |

EXAMPLE 16

By the methods of Examples 13 to 15, and as reported in Table 5 below, the compounds of this invention are shown to exhibit excellent activity against insects belonging to the Lepidoptera such as tobacco cutworm (*Prodenia litura*), rice stem borer (*Chilo suppressalis*), fall webworm (*Hyphantria cunea*) and the like, as compared with compounds of similar structure, identified by letters of the alphabet.

Table 5

| | Results of tests on harmful *Lepidoptera* insects Killing Ratio (%) | | | | | | |
|---|---|---|---|---|---|---|---|
| Compounds | Tobacco cutworm (*Prodenia litura*) | | | Rice-stem borer | Fall webworm (*Hyphantriacunea*) | | |
| | 1000 ppm | 300 ppm | 100 ppm | 250 ppm | 1000 ppm | 300 ppm | 100 ppm |
| 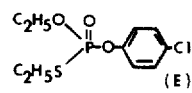 (E) | 30 | 10 | 0 | 0 | 0 | 0 | 0 |

Table 5-continued
Results of tests on harmful Lepidoptera insects
| Compounds | Killing Ratio (%) | | | | | | |
|---|---|---|---|---|---|---|---|
| | Tobacco cutworm (Prodenia litura) | | | Rice-stem borer | Fall webworm (Hyphantriacunea) | | |
| | 1000 ppm | 300 ppm | 100 ppm | 250 ppm | 1000 ppm | 300 ppm | 100 ppm |
| 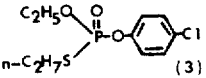 (3) | 100 | 100 | 100 | 100 | 100 | 100 | 100 |
| 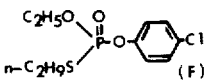 (F) | 0 | 0 | 0 | 0 | 40 | 0 | 0 |
| 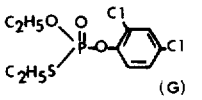 (G) | 30 | 5 | 0 | 0 | 0 | 0 | 0 |
| 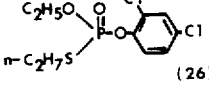 (26) | 100 | 100 | 100 | 100 | 100 | 100 | 100 |
| 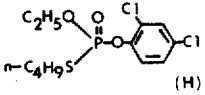 (H) | 10 | 0 | 0 | 0 | 50 | 0 | 0 |
| 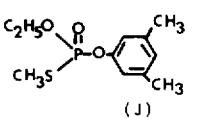 (J) | 0 | 0 | 0 | 0 | 0 | 0 | 0 |
| 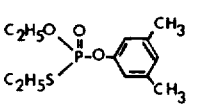 (K) | 10 | 0 | 0 | 0 | 20 | 0 | 0 |
| 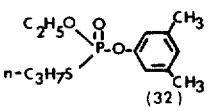 (32) | 100 | 100 | 100 | 100 | 100 | 100 | 100 |
| 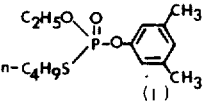 (I) | 10 | 0 | 0 | 0 | 0 | 0 | 0 |
| 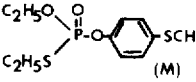 (M) | 40 | 0 | 0 | 0 | 30 | 0 | 0 |

Table 5-continued
Results of tests on harmful Lepidoptera insects
| Compounds | Killing Ratio (%) | | | | | | |
|---|---|---|---|---|---|---|---|
| | Tobacco cutworm (Prodenia litura) | | | Rice-stem borer | Fall webworm (Hyphantriacunea) | | |
| | 1000 ppm | 300 ppm | 100 ppm | 250 ppm | 1000 ppm | 300 ppm | 100 ppm |
| 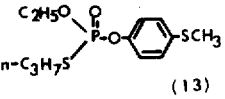 (13) | 100 | 100 | 100 | 100 | 100 | 100 | 90 |
| 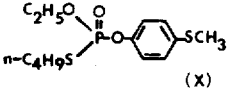 (X) | 50 | 0 | 0 | 0 | 40 | 0 | 0 |
| 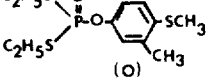 (O) | 50 | 0 | 0 | 0 | 40 | 0 | 0 |
| 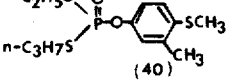 (40) | 100 | 100 | 100 | 96.4 | 100 | 100 | 100 |
| 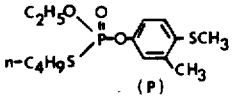 (P) | 50 | 0 | 0 | 0 | 50 | 0 | 0 |
| 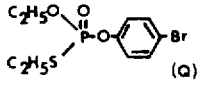 (Q) | 30 | 0 | 0 | 10 | 10 | 0 | 0 |
| 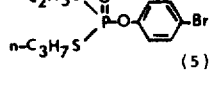 (5) | 100 | 100 | 100 | 100 | 100 | 80 | 60 |
| 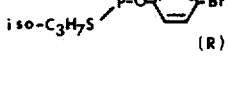 (R) | 10 | 0 | 0 | 0 | 20 | 0 | 0 |
| 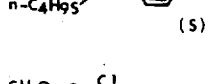 (S) | 0 | 0 | 0 | 0 | 0 | 0 | 0 |
|  (T) | 0 | 0 | 0 | 0 | 0 | 0 | 0 |
| 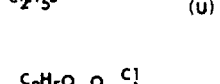 (U) | 10 | 0 | 0 | 0 | 0 | 0 | 0 |
|  (39) | 100 | 100 | 100 | 99 | 100 | 100 | 90 |

Table 5-continued

| Compounds | Results of tests on harmful Lepidoptera insects Killing Ratio (%) | | | | | | |
|---|---|---|---|---|---|---|---|
| | Tobacco cutworm (Prodenia litura) | | | Rice-stem borer | Fall webworm (Hyphantriacunea) | | |
| | 1000 ppm | 300 ppm | 100 ppm | 250 ppm | 1000 ppm | 300 ppm | 100 ppm |
| 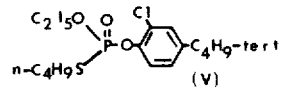 (V) | 10 | 0 | 0 | 0 | 10 | 0 | 0 |
| 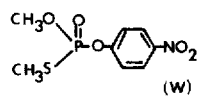 (W) | 20 | 0 | 0 | 0 | 10 | 0 | 0 |
| 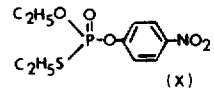 (X) | 60 | 20 | 0 | 12.3 | 30 | 0 | 0 |
| 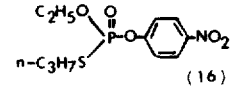 (16) | 100 | 100 | 100 | 98.6 | 100 | 100 | 90 |
| 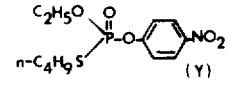 (Y) | 20 | 0 | 0 | 0 | 0 | 0 | 0 |
| 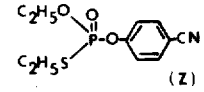 (Z) | 20 | 0 | 0 | 0 | 0 | 0 | 0 |
| 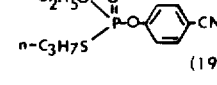 (19) | 100 | 100 | 100 | 100 | 100 | 90 | 40 |

EXAMPLE 17

Test against Green peach aphids (*Myzus persicae*) and Hop aphid (*Phorodon humuli*) (contact action)

Solvent: 3 parts by weight of aceotn
Emulsifier: 1 part by weight of alkyl aryl polyglycol ether To prepare a suitable preparation of active compound, 1 part by weight of the active compound is mixed with the stated amount of solvent containing the stated amount of emulsifier and the concentrate is diluted with water to the desired concentration.

Cabbage plant infested with each aphids are sprayed with the preparation of the active compound until dripping wet. After 24 hours, the degree of destruction is determined as a percentage: 100% means that all the aphids are killed whereas 0% means that none are killed.

The results are shown in Table 6.

Table 6

| | Results of tests on Green peach aphid and Hop aphid | | | |
|---|---|---|---|---|
| | Concentration of a.i. (%) | Green peach aphid | | Hop aphid |
| | | A | B | A | B |
| 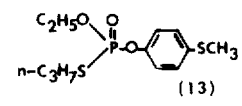 (13) Compound No. 13 of the present invention | 0.1 | 100% | — | 100% | — |
| | 0.02 | 100 | 100% | 100 | 100% |
| | 0.004 | 100 | 100 | 100 | 100 |
| | 0.0008 | 90 | 100 | 90 | 100 |
| | 0.00016 | 5 | 93 | 25 | 100 |
| | 0.000032 | — | 0 | — | 93 |

Table 6-continued

Results of tests on Green peach aphid and Hop aphid

| | Concentration of a.i. (%) | Green peach aphid A | B | Hop aphid A | B |
|---|---|---|---|---|---|
| $C_2H_5O$, $O$, $Cl$ structure with $P-O$-phenyl-$Cl$, $n-C_3H_7S$ (26) | 0.1 | 100% | — | 100% | — |
| | 0.02 | 100 | 100% | 100 | 100% |
| | 0.004 | 100 | 100 | 80 | 100 |
| | 0.0008 | 80 | 75 | 50 | 100 |
| | 0.00016 | 30 | 50 | 25 | 93 |
| Compound No. 26 of the present invention | 0.000032 | — | 5 | — | 70 |
| $CH_3O$, $S$ structure $P-O$-phenyl-$SCH_3$, $CH_3O$, $CH_3$ | 0.1 | 85% | — | 85% | — |
| | 0.02 | 80 | 100% | 70 | 100% |
| | 0.004 | 70 | 98 | 40 | 100 |
| | 0.0008 | 15 | 70 | 25 | 98 |
| | 0.00016 | 5 | 40 | 10 | 80 |
| Commercial control: lebaycid (D) | 0.000032 | — | 10 | — | 30 |

*A: Resistance-acquired Green peach aphid and Hop aphid
**B: Green peach aphid and Hop aphid without resistance

EXAMPLE 18

Carmine mite or two-spotted spider mite (*Tetranychus telarius* test)

Testing method

A haricot bean having two developing leaves planted in a 6 cm diameter pot was infected with 50 – 100 imagines and nymphs of carmine mite. Two days after the infection, 40 ml of the preparation of the active compound diluted to the prescribed concentration prepared in the same manner as in Example 13 were sprayed on to the pot. The pot was kept in a greenhouse for 10 days, and the control effect was evaluated. The evaluation is expressed by an index of the following scale:

Control Effect Index

3: No living imago or nymph
2: Less than 5% living imagines and nymphs based on the untreated control
1: 6 – 50% of living imagines and nymphs based on the untreated control
0: more than 51% of living imagines and nymphs based on the untreated control The results are shown in Table 7.

Table 7

Test results against *Tetranychus telarius* larvae

| Compound No. | Control Effect Active Ingredient Concentration | | |
|---|---|---|---|
| | 1000 ppm | 300 ppm | 100 ppm |
| 13 | 3 | 3 | 3 |
| 16 | 3 | 3 | 2 |
| 17 | 3 | 3 | 2 |
| 20 | 3 | 3 | 3 |
| 21 | 3 | 3 | 3 |
| 23 | 3 | 3 | 2 |
| 24 | 3 | 3 | 2 |
| 44 | 3 | 3 | 2 |
| 49 | 3 | 3 | 3 |
| CPCBS* (comparison) | 3 | 2 | 0 |
| CMP** (comparison) | 3 | 1 | 0 |
| Untreated Control | 0 | 0 | 0 |

*CPCBS (Wettable Powder): p-chlorophenyl-p'chlorobenzenesulfonate 36%; bis(4-chlorophenoxy)metan 14%
**CMP: O,O-diethyl-S-(2,5-dichlorophenylmercaptomethyl)dithiophosphate

EXAMPLE 19

House fly (*Musca domestica*) test

Testing method 1 ml of an emulsion of the active compound diluted to the prescribed concentration prepared in the same manner as in Example 13 was applied on to a filter paper placed in a Petri dish of 9 cm diameter. 10 mature female adult house flies were then placed in the dish and the dish was kept in a constant temperature chamber at 28°C. After 24 hours, the number of dead insects was counted and the killing ratio was calculated.

The results are shown in Table 8.

Table 8

Test results against *Musca domestica* adults

| Compound No. | Killing Ratio (%) Active Ingredient Concentration | | |
|---|---|---|---|
| | 1000 ppm | 100 ppm | 10 ppm |
| 13 | 100 | 100 | 80 |
| 14 | 100 | 100 | — |
| 15 | 100 | 100 | — |
| 16 | 100 | 100 | — |
| 18 | 100 | 100 | — |
| 19 | 100 | 100 | — |
| 20 | 100 | 100 | — |
| 21 | 100 | 100 | — |
| 40 | 100 | 100 | — |
| 41 | 100 | 100 | — |
| 49 | 100 | 100 | 70 |
| 50 | 100 | 100 | 80 |

Table 8-continued

| Compound No. | Test results against *Musca domestica* adults Killing Ratio (%) Active Ingredient Concentration | | |
|---|---|---|---|
| | 1000 ppm | 100 ppm | 10 ppm |
| 62 | 100 | 100 | — |
| DEP (comparison) | 100 | 100 | — |
| Untreated Control | 0 | 0 | 0 |

It will be appreciated that the instant specification and examples are set forth by way of illustration and not limitation, and that various modifications and changes may be made without departing from the spirit and scope of the present invention.

What is claimed is:
1. A phosphoric acid ester of the formula

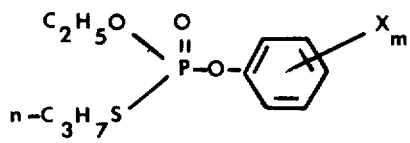

wherein
at least one X is nitro, cyano, lower alkylmercapto, lower alkylsulfinyl, lower alkoxycarbonyl, or lower alkylcarbonyl, and the others if present may also be halogen or lower alkyl, and
$m$ is 1, 2 or 3.

2. The compound according to claim 1, wherein such compound is O-ethyl-O-(4-methylmercaptophenyl)-S-n-propyl phosphorothiolate of the formula

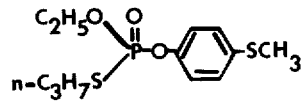

3. The compound according to claim 1, wherein such compound is O-ethyl-O-(4-nitrophenyl)-S-n-propyl phosphorothiolate of the formula

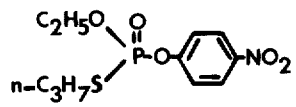

4. The compound according to claim 1, wherein such compound is O-ethyl-O-4-cyanophenyl)-S-n-propyl phosphorothiolate of the formula

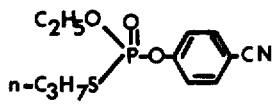

5. The compound according to claim 1, wherein such compound is O-ethyl-O-(3-methyl-4-methylmercaptophenyl)-S-n-propyl phosphorothiolate of the formula

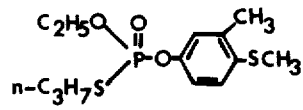

6. The compound according to claim 1, wherein such compound is O-ethyl-O-(3-methyl-4-nitrophenyl)-S-n-propyl phosphorothiolate of the formula

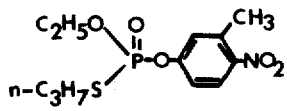

7. The compound according to claim 1, wherein such compound is O-ethyl-O-(2-methylmercaptophenyl)-S-n-propyl phosphorothiolate of the formula

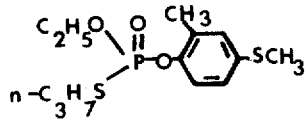

8. The compound according to claim 1, wherein such compound is O-ethyl-O(3,5-dimethyl-4-methylmercaptophenyl)-S-n-propyl phosphorothiolate of the formula

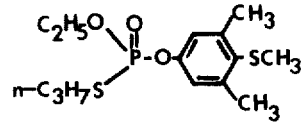

* * * * *